US008999882B2

(12) United States Patent
Lockemeyer et al.

(10) Patent No.: US 8,999,882 B2
(45) Date of Patent: Apr. 7, 2015

(54) PROCESS FOR TREATING A CARRIER, A PROCESS FOR PREPARING A CATALYST, THE CATALYST, AND USE OF THE CATALYST

(71) Applicant: Shell Oil Company, Houston, TX (US)

(72) Inventors: John Robert Lockemeyer, Sugar Land, TX (US); Randall Clayton Yeates, Sugar Land, TX (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 13/931,081

(22) Filed: Jun. 28, 2013

(65) Prior Publication Data

US 2013/0289288 A1 Oct. 31, 2013

Related U.S. Application Data

(62) Division of application No. 11/940,968, filed on Nov. 15, 2007, now Pat. No. 8,501,664.

(60) Provisional application No. 60/866,577, filed on Nov. 20, 2006.

(51) Int. Cl.
| | | |
|---|---|---|
| *B01J 23/68* | (2006.01) | |
| *B01J 23/50* | (2006.01) | |
| *C07C 213/00* | (2006.01) | |
| *C07C 29/00* | (2006.01) | |
| *C07C 41/02* | (2006.01) | |
| *C07D 301/04* | (2006.01) | |
| *B01J 27/06* | (2006.01) | |
| *B01J 27/14* | (2006.01) | |
| *B01J 27/24* | (2006.01) | |
| *B01J 27/02* | (2006.01) | |
| *B01J 32/00* | (2006.01) | |
| *B01J 37/06* | (2006.01) | |
| *C07D 301/10* | (2006.01) | |

(52) U.S. Cl.
CPC .............. *B01J 23/688* (2013.01); *B01J 23/50* (2013.01); *B01J 32/00* (2013.01); *B01J 37/06* (2013.01); *C07D 301/10* (2013.01); *C07C 29/00* (2013.01); *C07C 41/02* (2013.01); *C07C 213/00* (2013.01); *C07D 301/04* (2013.01)

(58) Field of Classification Search
USPC ......... 502/348, 302, 439, 347, 200, 216, 201, 502/208, 202, 224, 340, 317, 324, 306; 564/503; 568/680, 861, 956, 852; 423/628; 549/534, 536
See application file for complete search history.

(56) References Cited

U.S. PATENT DOCUMENTS

| | | | |
|---|---|---|---|
| 2,424,083 A | 7/1947 | Finch | |
| 2,671,764 A | 3/1954 | Sacken | 252/440 |
| 2,769,016 A | 10/1956 | Lichtenwalter et al. | 260/348.5 |
| 2,901,441 A | 8/1959 | Waterman | |
| 3,563,913 A | 2/1971 | Krijger et al. | 252/463 |
| 3,563,914 A | 2/1971 | Wattimena | 252/463 |
| 3,895,093 A | 7/1975 | Weidenbach et al. | |
| 3,950,507 A | 4/1976 | Kuklina et al. | 423/626 |
| 3,972,829 A | 8/1976 | Michalko | |
| 4,005,049 A | 1/1977 | Fields | |
| 4,125,480 A | 11/1978 | Maxwell | |
| 4,186,106 A | 1/1980 | Rebsdat et al. | |
| 4,212,772 A | 7/1980 | Mross et al. | |
| 4,235,798 A | 11/1980 | Bartley et al. | |
| 4,244,889 A | 1/1981 | Bartley et al. | |
| 4,356,312 A | 10/1982 | Nielsen et al. | |
| 4,361,500 A | 11/1982 | Mathe et al. | |
| 4,361,504 A | 11/1982 | Solomon et al. | |
| 4,366,092 A | 12/1982 | Winterton | |
| 4,367,167 A | 1/1983 | Lee et al. | |
| 4,368,144 A | 1/1983 | Mitsuhata et al. | |
| 4,379,134 A | 4/1983 | Weber et al. | 423/626 |
| 4,382,149 A | 5/1983 | Krueger | |
| 4,420,420 A | 12/1983 | Mita et al. | |
| 4,532,231 A | 7/1985 | Johnson | |
| 4,628,129 A | 12/1986 | Bartley | |
| 4,665,048 A | 5/1987 | Van Leeuwen et al. | |
| 4,761,394 A | 8/1988 | Lauritzen | 502/348 |
| 4,766,105 A | 8/1988 | Lauritzen | 502/216 |
| 4,797,270 A | 1/1989 | Alvarado Cendan et al. | 423/625 |

(Continued)

FOREIGN PATENT DOCUMENTS

| | | | |
|---|---|---|---|
| AU | 757495 | 4/2000 | |
| EP | 0003642 | 7/1984 | C07D 301/10 |

(Continued)

OTHER PUBLICATIONS

"Kirk-Othmer Encyclopedia of Chemical Technology", 3rd edition, vol. 9, 1980, pp. 445-447.
Brunauer, Emmett and Teller, Journal of the American chemical society 60 (1938) pp. 309-316.
F F Y Wang (Ed.), "Treatise on materials Science and Technology", vol. 9 (NY, 1976) pp. 79-81.
J S Reed "Introduction to the Principles of Ceramic Processing", (NY 1988) pp. 152 ff.

(Continued)

Primary Examiner — Elizabeth Wood

(57) ABSTRACT

A process for treating a carrier, or a precursor thereof, to at least partly remove impurities from the carrier, or the precursor thereof, comprising: contacting the carrier, or the precursor thereof, with a treatment solution comprising a salt in a concentration of at most 0.05 molar, wherein the salt comprises a cation and an anion, and wherein the cation is selected from ammonium, phosphonium, organic cations and combinations thereof, and wherein the anion is selected from organic anions, inorganic carboxylates, oxyanions of elements from Groups IIIA through VIIA of the Periodic Table of Elements, and combinations thereof; and separating at least part of the treatment solution from the carrier, or the precursor thereof.

17 Claims, No Drawings

(56) References Cited

U.S. PATENT DOCUMENTS

| | | | |
|---|---|---|---|
| 4,797,279 A | 1/1989 | Karamata et al. | |
| 4,810,689 A | 3/1989 | Hayden | |
| 4,822,900 A | 4/1989 | Hayden | 549/534 |
| 4,845,296 A | 7/1989 | Ahmed et al. | 564/477 |
| 4,874,739 A | 10/1989 | Boxhoorn | |
| 4,886,917 A | 12/1989 | Knopf et al. | |
| 4,908,343 A | 3/1990 | Bhasin | 502/218 |
| 4,916,243 A | 4/1990 | Bhasin et al. | |
| 4,994,587 A | 2/1991 | Notermann et al. | |
| 4,994,588 A | 2/1991 | Kapicak et al. | |
| 4,994,589 A | 2/1991 | Notermann | 549/534 |
| 5,037,794 A | 8/1991 | Magistro | |
| 5,055,442 A | 10/1991 | Osaka et al. | |
| 5,057,481 A | 10/1991 | Bhasin | |
| 5,100,859 A | 3/1992 | Gerdes et al. | |
| 5,102,848 A | 4/1992 | Soo et al. | 502/218 |
| 5,112,795 A | 5/1992 | Minahan et al. | |
| 5,157,180 A | 10/1992 | West et al. | |
| 5,179,057 A | 1/1993 | Bartley | |
| 5,187,140 A | 2/1993 | Thorsteinson et al. | |
| 5,189,004 A | 2/1993 | Bartley | |
| 5,280,697 A | 1/1994 | Miller | |
| 5,364,826 A | 11/1994 | Kemp | |
| 5,374,748 A | 12/1994 | Rizkalla | |
| 5,380,697 A | 1/1995 | Matusz et al. | 502/348 |
| 5,380,885 A | 1/1995 | Kemp | |
| 5,387,751 A | 2/1995 | Hayden et al. | |
| 5,418,202 A | 5/1995 | Evans et al. | |
| 5,447,897 A | 9/1995 | Kemp | |
| 5,486,628 A | 1/1996 | Kemp | |
| 5,545,603 A | 8/1996 | Kemp | |
| 5,597,773 A | 1/1997 | Evans et al. | |
| 5,663,385 A | 9/1997 | Kemp | |
| 5,668,077 A | 9/1997 | Klopries et al. | |
| 5,703,253 A | 12/1997 | Evans | |
| 5,734,068 A | 3/1998 | Klopries et al. | |
| 5,739,075 A | 4/1998 | Matusz | 502/302 |
| 5,801,259 A | 9/1998 | Kowaleski | 549/536 |
| 5,935,894 A | 8/1999 | Kanazirev | |
| 6,103,916 A | 8/2000 | Takada et al. | 549/534 |
| 6,281,160 B1 | 8/2001 | Basset et al. | |
| 6,368,998 B1 | 4/2002 | Lockemeyer | 502/347 |
| 6,579,825 B2 | 6/2003 | Lockemeyer | |
| 6,656,874 B2 | 12/2003 | Lockemeyer | |
| 6,750,173 B2 | 6/2004 | Rizkalla et al. | 502/348 |
| 6,846,774 B2 | 1/2005 | Rizkalla | 502/348 |
| 6,858,560 B2 | 2/2005 | Rizkalla | 502/202 |
| 6,939,979 B2 | 9/2005 | Rizkalla et al. | 549/533 |
| 6,987,080 B2 | 1/2006 | Schmitz | 503/348 |
| 7,232,786 B2 | 6/2007 | Lockemeyer | |
| 7,232,918 B2 | 6/2007 | Lockemeyer | |
| 7,247,600 B2 | 7/2007 | Lockemeyer | |
| 7,504,525 B2 | 3/2009 | Lockemeyer | |
| 2002/0010094 A1 | 1/2002 | Lockemeyer | 502/439 |
| 2003/0162655 A1 | 8/2003 | Szymanski et al. | |
| 2004/0049061 A1 | 3/2004 | Lockemeyer et al. | 549/536 |
| 2005/0085649 A1 | 4/2005 | Lockemeyer | |
| 2005/0222442 A1 | 10/2005 | Lockemeyer | |
| 2006/0252643 A1 | 11/2006 | Pak | |
| 2007/0191618 A1 | 8/2007 | Lockemeyer | |
| 2007/0207914 A1 | 9/2007 | Lockemeyer | |
| 2007/0208186 A1 | 9/2007 | Lockemeyer | |
| 2008/0125610 A1 | 5/2008 | Lockemeyer | |

FOREIGN PATENT DOCUMENTS

| | | | |
|---|---|---|---|
| EP | 0211521 | 2/1987 | |
| EP | 266015 | 12/1991 | B01J 23/68 |
| EP | 563414 | 10/1993 | |
| EP | 0003642 | 7/1994 | |
| EP | 716884 | 6/1996 | B01J 23/66 |
| EP | 0937498 | 8/1999 | |
| FR | 2005978 | 12/1969 | |
| GB | 568978 | 1/1946 | |
| GB | 1601635 | 11/1981 | |
| JP | 5301191 | 1/1978 | |
| JP | 56105750 | 8/1981 | |
| JP | 56164013 | 12/1981 | |
| JP | 4346835 | 2/1992 | B01J 23/66 |
| JP | 8224477 | 3/1996 | |
| JP | 9500571 | 1/1997 | |
| WO | 8606063 | 10/1986 | |
| WO | 9511953 | 5/1995 | |
| WO | 9623585 | 8/1996 | |
| WO | 9641848 | 12/1996 | |
| WO | 9713579 | 4/1997 | |
| WO | 9800413 | 1/1998 | |
| WO | 0015333 | 3/2000 | |
| WO | 0015334 | 3/2000 | |
| WO | 0015335 | 3/2000 | |
| WO | WO0015333 | 3/2000 | B01J 23/50 |
| WO | WO0015334 | 3/2000 | B01J 23/50 |
| WO | WO0015335 | 3/2000 | B01J 23/50 |
| WO | 03074171 | 9/2003 | |

OTHER PUBLICATIONS

Brunauer, S., et al., "Absorption of Glass in Multimolecular Layers", Journal of the American Chemical Society, 1938, vol. 60, pp. 309-316.

Kirk-Othmer, 'Enamels, Porcelain or Vitreous to Ferrites', Encyclopedia of Chemical Technology, 3rd Ed., vol. 9, pp. 445-447.

Reed, J.S., "Flocculants, Binders, and Bonds", Binder Compositions, Chapter 11.1, Introduction to the Principles of Ceramic Processing, 1998, pp. 152-173.

Wang, F.F.Y., "Treatise on Materials Science and Technology", 1976, vol. 9, Ceramic Fabrication Processes, pp. 79-81.

US 8,999,882 B2

PROCESS FOR TREATING A CARRIER, A PROCESS FOR PREPARING A CATALYST, THE CATALYST, AND USE OF THE CATALYST

CROSS-REFERENCE TO RELATED APPLICATIONS

This application is a divisional of U.S. application Ser. No. 11/940,968, filed Nov. 15, 2007, which claims the benefit of U.S. Provisional Application No. 60/866,577, filed Nov. 20, 2006, which are both incorporated herein by reference.

FIELD OF THE INVENTION

The invention relates to a process for treating a carrier, a process for preparing a catalyst, and the catalyst which is obtained by the process. The invention also relates to a process for the epoxidation of an olefin, which process comprises contacting an epoxidation feed comprising the olefin and oxygen with the catalyst. The invention also relates to a process which uses the olefin oxide so produced for making a 1,2-diol, a 1,2-diol ether or an alkanolamine.

BACKGROUND OF THE INVENTION

In olefin epoxidation, a feed containing an olefin and an oxygen source is contacted with a catalyst under epoxidation conditions. The olefin is reacted with oxygen to form an olefin oxide. A product mix results that contains olefin oxide and, typically, unreacted feed and combustion products.

The olefin oxide may be reacted with water to form a 1,2-diol, with an alcohol to form a 1,2-diol ether, or with an amine to form an alkanolamine. Thus, 1,2-diols, 1,2-diol ethers, and alkanolamines may be produced in a multi-step process initially comprising olefin epoxidation and then the conversion of the formed olefin oxide with water, an alcohol, or an amine.

Olefin epoxidation catalysts comprise a silver component, usually with one or more additional elements deposited therewith, on a carrier. The presence of certain species contained in the carrier of the catalyst can be detrimental to the deposition process of catalytic species and/or catalyst performance. Various patents have focused on the pretreatment of carriers to improve the performance of a catalyst.

For example, U.S. Pat. No. 6,368,998-B1 shows that lowering the concentration of one or more ionizable species on the surface of a carrier and/or in the one or more materials used to make the carrier improves the performance of a catalyst in an epoxidation process. The concentration of ionizable species may be lowered by removing the species, rendering the species insoluble, or rendering the species immobile. Removal of the ionizable species may include contacting the carrier with de-ionized water as well as aqueous and/or organic solvent-based solutions containing tetraethylammonium hydroxide, ammonium acetate, lithium carbonate, barium acetate, strontium acetate, crown ether, methanol, ethanol, dimethylformamide, and mixtures thereof.

U.S. Pat. No. 6,750,173-B2 shows that pretreatment of a carrier to remove sodium and partially replace the sodium with lithium improves the stability of a catalyst made from such carrier in an epoxidation process.

The catalyst performance may be assessed on the basis of selectivity, activity and stability of operation. The selectivity is the fraction of the converted olefin yielding the desired olefin oxide. As the catalyst ages, the fraction of the olefin converted normally decreases with time and to maintain a constant level of olefin oxide production (e.g., work rate) the temperature of the reaction may be increased. However, this adversely affects the selectivity of the conversion to the desired olefin oxide. In addition, the equipment used can tolerate temperatures only up to a certain level so that it is necessary to terminate the reaction when the reaction temperature reaches a level inappropriate for the reactor. Thus the longer the activity and selectivity can be maintained at acceptable values, the longer the catalyst charge can be kept in the reactor and the more product is obtained. Quite modest improvements in the selectivity and maintenance of the selectivity and activity over long periods yield substantial dividends in terms of process efficiency.

SUMMARY OF THE INVENTION

According to one embodiment of the present invention, there is provided a process for treating a carrier, or a precursor thereof, to at least partly remove impurities from the carrier, or the precursor thereof, comprising: contacting the carrier, or the precursor thereof, with a treatment solution comprising a salt in a concentration of less than 0.015 molar at a temperature of greater than 40° C., wherein the salt comprises an anion selected from halides, organic anions, inorganic carboxylates, oxyanions of elements from Groups IIIB to VIIB, Group IIIA, and Groups VA to VIIA of the Periodic Table of Elements, cyanate, isocyanate, cyanide, and combinations thereof; and separating at least part of the treatment solution from the carrier, or the precursor thereof.

According to another embodiment of the present invention, there is provided a process for treating a carrier, or a precursor thereof, to at least partly remove impurities from the carrier, or the precursor thereof, comprising: contacting the carrier, or the precursor thereof, with a treatment solution comprising a salt in a concentration of at most 0.05 molar, wherein the salt comprises a cation and an anion, and wherein the cation is selected from ammonium, phosphonium, organic cations and combinations thereof, and wherein the anion is selected from organic anions, inorganic carboxylates, oxyanions of elements from Groups IIIA through VIIA of the Periodic Table of Elements, and combinations thereof; and separating at least part of the treatment solution from the carrier, or the precursor thereof.

The invention also provides a process for preparing a catalyst and the catalyst obtained by the preparation process.

The invention also provides a process for the epoxidation of an olefin comprising reacting the olefin with oxygen in the presence of a catalyst prepared according to this invention.

Further, the invention provides a process of preparing a 1,2-diol, a 1,2-diol ether or an alkanolamine comprising obtaining an olefin oxide by the process for the epoxidation of an olefin according to this invention, and converting the olefin oxide into the 1,2-diol, the 1,2-diol ether or the alkanolamine.

DETAILED DESCRIPTION OF THE INVENTION

Impurities present in a carrier can adversely affect the performance of a catalyst, and therefore, efforts are made to reduce the amount of impurities as much as is practicably possible. Typically, impurities present in the carrier may include sodium, potassium, aluminates, soluble silicate, calcium, magnesium, aluminosilicate, cesium, lithium, and combinations thereof. It has been found that the efficiency of removing impurities in the carrier can be improved by contacting the carrier with a solution containing a salt in a low concentration. When a catalyst is prepared in accordance with this invention, an advantage can be realized in the performance of the catalyst as compared to a catalyst prepared using a carrier which has not been subjected to the inventive treatment. The advantage may be found, for example, in an improved selectivity, activity, and/or an improved resistance against performance decline, in particular activity and selectivity. It is unexpected that treating a carrier, or a precursor thereof, with a solution containing a salt in a low concentration results in a catalyst which is advantaged over catalysts prepared using carriers which have been subjected to washing with water or a solution containing the salt in a higher concentration.

The carrier for use in this invention may comprise natural or artificial inorganic particulate materials which may include refractory materials, silicon carbide, clays, zeolites, charcoal and alkaline earth metal carbonates, for example calcium carbonate or magnesium carbonate. Preferred are refractory materials, for example alumina, magnesia, zirconia and silica. The most preferred material is α-alumina. Typically, the carrier may comprise at least 85 wt %, more typically 90 wt %, in particular 95 wt % α-alumina or a precursor thereof, frequently up to 99.9 wt %, or even up to 100 wt %, α-alumina or a precursor thereof. The α-alumina may be obtained by mineralization of α-alumina, suitably by boron or, preferably, fluoride mineralization. Reference is made to U.S. Pat. Nos. 3,950,507, 4,379,134 and 4,994,589, which are incorporated herein by reference for descriptions relating to the mineralization of α-alumina.

The term "precursors" of the carrier as used herein is meant to include the formed or shaped greenware prior to calcining as well as the starting materials that are formed or shaped into the greenware. Starting materials may include α-alumina, α-alumina precursors, burnout material, and bond material. The α-alumina precursors include hydrated aluminas, for example boehmite, pseudoboehmite, and gibbsite, as well as transition aluminas, for example the chi, kappa, gamma, delta, theta, and eta aluminas. The bond material may be based on a silica-containing composition comprising a crystallization inhibitor, inhibiting the formation of crystalline silica-containing compositions. The silica-containing compositions for use as a bond material may comprise an alkali metal silicate bond material, or preferably an alkaline earth metal silicate bond material. The bond material may further comprise a hydrated alumina and optionally a titanium component and/or a zirconium component. Burnout materials are well known in the art (cf., for example, F F Y Wang (Ed.), "Treatise on Materials Science and Technology", Volume 9, (New York, 1976), pp. 79-81; or J S Reed, "Introduction to the Principles of Ceramic Processing", (New York, 1988), pp. 152 ff.).

The carrier may preferably have a surface area of at most 20 m²/g, in particular in the range of from 0.1 to 20 m²/g, more in particular from 0.5 to 10 m²/g, preferably 1 to 3 m²/g and more preferably 1.3 to 2.6 m²/g. "Surface area" as used herein is understood to refer to the surface area as determined by the BET (Brunauer, Emmett and Teller) method as described in Journal of the American Chemical Society 60 (1938) pp. 309-316.

In an embodiment, the alumina carrier has a surface area of at least 1 m²/g, and a pore size distribution such that pores with diameters in the range of from 0.2 to 10 μm represent at least 70% of the total pore volume and such pores together provide a pore volume of at least 0.25 ml/g, relative to the weight of the carrier. Preferably, in this particular embodiment, the pore size distribution may be such that pores with diameters less than 0.2 μm represent from 0.1 to 10% of the total pore volume, in particular from 0.5 to 7% of the total pore volume; the pores with diameters in the range of from 0.2 to 10 μm represent from 80 to 99.8% of the total pore volume, in particular from 85 to 99% of the total pore volume; and the pores with diameters greater than 10 μm represent from 0.1 to 20% of the total pore volume, in particular from 0.5 to 10% of the total pore volume. In this particular embodiment, the pores with diameters in the range of from 0.2 to 10 μm preferably provide a pore volume in the range of from 0.3 to 0.8 ml/g, in particular from 0.35 to 0.7 ml/g, and the total pore volume of the carrier may be in the range of from 0.3 to 0.8 ml/g, in particular from 0.35 to 0.7 ml/g.

In another embodiment, the alumina carrier has a surface area of at least 1 m²/g, and a pore size distribution such that at least 80% of the total pore volume may be contained in pores with diameters in the range of from 0.1 to 10 μm, and at least 80% of the pore volume contained in the pores with diameters in the range of from 0.1 to 10 μm may be contained in pores with diameters in the range of from 0.3 to 10 μm. Preferably, in this particular embodiment, the pore size distribution may be such that pores with diameters less than 0.1 μm represent at most 5% of the total pore volume, in particular at most 1% of the total pore volume; the pores with diameters in the range of from 0.1 to 10 μm represent less than 99% of the total pore volume, in particular less than 98% of the total pore volume; the pores with diameters in the range of from 0.3 to 10 μm represent at least 85%, in particular at least 90% of the pore volume contained in the pores with diameters in the range of from 0.1 to 10 μm; the pores with diameters less than 0.3 μm represent from 0.01 to 10% of the total pore volume, in particular from 0.1 to 5% of the total pore volume; and the pores with diameters greater than 10 μm represent from 0.1 to 10% of the total pore volume, in particular from 0.5 to 8% of the total pore volume. In this particular embodiment, the pore size distribution preferably is such that the median pore diameter may be in the range of from 0.8 to 1.9 μm, in particular 0.9 to 1.8 μm.

As used herein, the pore size distribution and the pore volumes are as measured by mercury intrusion to a pressure of 3.0×10⁸ Pa using a Micromeretics Autopore 9200 (130° contact angle, mercury with a surface tension of 0.473 N/m, and correction for mercury compression applied).

As used herein, the median pore diameter is the pore diameter at which half of the total pore volume is contained in pores having a larger pore diameter and half of the total pore volume is contained in pores having a smaller pore diameter.

As used herein, pore volume (ml/g), and surface area (m2/g) and water absorption (%) are defined relative to the weight of the carrier, unless stated otherwise.

According to the invention, the carrier, or the precursor thereof, is subjected to a treatment process. The treatment process comprises contacting the carrier, or the precursor thereof, with a treatment solution. The carrier, or the precursor thereof, may be contacted with the treatment solution in a continuous or batch fashion. When the contact is conducted in a continuous fashion, the treatment solution may be recirculated or all or a part of the treatment solution may be replaced with additional fresh treatment solution. The contact may be conducted with or without stirring. After contact, the treatment solution may be at least partly separated from the carrier, or the precursor thereof. Preferably, at least 25 wt %, more preferably at least 35 wt %, most preferably at least 50 wt %, of the treatment solution may be separated from the carrier. The contacting and separating steps may be repeated one or more times. For each of the contacting steps, the composition of the treatment solution may comprise the same salt composition or a different salt composition.

The pressure during contact is not critical to the treatment process. The pressure may be any pressure including sub atmospheric, atmospheric and super atmospheric pressure. Preferably, the contact may be conducted at atmospheric pressure.

A suitable temperature for contacting the carrier, or precursor thereof, with the treatment solution may be a temperature of greater than 15° C., preferably greater than 40° C., more preferably greater than 75° C., most preferably greater than 85° C. The temperature for contacting the carrier, or the precursor thereof, with the treatment solution may be in the range of from 15° C. to 120° C. Preferably, at least one contacting step may comprise contacting the carrier, or the precursor thereof, with a treatment solution at a temperature in the range of from 75° C. to 120° C., more preferably from greater than 85° C. to 110° C., most preferably from 90° C. to 110° C. Preferably, the treatment process may comprise contacting the carrier, or the precursor thereof, with a treatment solution at a temperature in the range of from 75° C. to 120° C., and subsequently contacting the carrier, or the precursor thereof, with an additional treatment solution at a temperature in the range of from 15° C. to 40° C., preferably from 20° C. to 35° C., for example 20° C., 25° C. or 30° C. More preferably, the treatment process may further comprise a third contacting step comprising contacting the carrier, or the precursor thereof, with a further treatment solution at a temperature in the range of from 15° C. to 40° C., preferably from 20° C. to 35° C., for example 20° C., 25° C. or 30° C. The treatment solution, additional treatment solution and further treatment solution may comprise the same salt composition or different salt compositions.

A suitable time for each contacting step may be at least 5 minutes, preferably at least 10 minutes. Preferably, the contact time for at least one contacting step may be in the range of from 0.5 to 48 hours, in particular from 1 to 24 hours. Preferably, at least one contacting step may have a contact time in the range of from 0.5 to 48 hours, and subsequently at least one contacting step may have a contact time in the range of from 0.15 to 24 hours, preferably from 0.2 to 6 hours.

For each contacting step, the mass ratio of treatment solution to carrier, or the precursor thereof, may be at least 1, in particular at least 1.2, more in particular at least 1.25. The mass ratio of treatment solution to carrier, or the precursor thereof, may be at most 20, in particular at most 10, more in particular at most 5. The mass ratio of treatment solution to carrier, or the precursor thereof, may be in the range of from 1 to 20, in particular from 1.2 to 5, more in particular from 1.25 to 2.

Soluble impurities present in the carrier such as sodium, potassium, aluminates, soluble silicate, calcium, magnesium, aluminosilicate, cesium, lithium and combinations thereof are at least partly removed by the treatment process. In particular, the treatment process may remove at least 10 wt % of the impurities, preferably at least 25 wt % of the impurities, more preferable at least 30 wt % of the impurities present in the carrier. More in particular, the treatment process may remove more than 50 wt % of the soluble sodium impurities, preferably more than 60 wt % of the soluble sodium impurities present in the carrier.

The treatment solution comprises a salt and a diluent. The salt comprises a cation and an anion. The diluent may be water, an alcohol or mixtures thereof. The alcohol preferably has in the molecular structure one or more carbon atoms, in particular from 2 to 6 carbon atoms. Preferably, the treatment solution may be an aqueous solution. The salt may be combined with the diluent or created in situ. As an example of in situ formation of the salt, acetic acid and ammonium bicarbonate may be combined with water resulting in a treatment solution comprising ammonium acetate and water. As another example of in situ formation of the salt, nitric acid and ammonium hydroxide may be combined with water resulting in a treatment solution comprising ammonium nitrate and water.

The salt may be any salt compound and may also be a combination of more than one salt. The salt may be present in the treatment solution in a concentration of at most 0.05 molar (moles of salt per liter of treatment solution). The pH of the treatment solution may be in the range of from 4 to 8, preferably in the range of from 5 to 7, more preferably in the range of from 5.5 to 6.5, as measured at 25° C.

In a first embodiment, the salt may comprise any cation, preferably a cation selected from Group IA metals, Group IIA metals, and combinations thereof. Preferably, the Group IA metal cations may be selected from sodium, lithium, potassium, cesium, and combinations thereof, more preferably lithium. Preferably, the Group IIA metal cations may be selected from magnesium, calcium, strontium, barium, and combinations thereof, more preferably magnesium.

The anion of the salt may be selected from halides, organic anions, inorganic carboxylates, oxyanions of elements from Groups IIIB to VIIB, Group IIIA, and Groups VA to VIIA of the Periodic Table of Elements (as defined as the CAS version in the Periodic Table of Elements in the "CRC Handbook of Chemistry and Physics", 69th ed. (CRC Press Inc. 1988)), cyanate, isocyanate, cyanide, and combinations thereof. Preferably, the halide may be selected from fluoride, chloride, bromide, and combinations thereof, more preferably chloride. Preferably, the oxyanions may be of elements from Group IIIA and Groups VA to VIIA of the Periodic Table of Elements. The oxyanions of elements from Group IIIA and Groups VA to VIIA may be selected from borate, metaborate, tetraborate, tetrafluoroborate, chlorate, perchlorate, bromate, perbromate, phosphate, metaphosphate, orthophosphate, hydrogenphosphate, dihydrogenphosphate, fluorophosphates, phosphite, hydrogenphosphite, sulfate, disulfate, hydrogensulfate, thiosulfate, sulfite, disulfite, hydrogensulfite, thiosulfite, nitrate, nitrite, and combinations thereof. Preferably, the oxyanions may be of elements from Group VA, in particular phosphate, metaphosphate, orthophosphate, hydrogenphosphate, dihydrogenphosphate, fluorophosphates, phosphite, hydrogenphosphite, nitrate, nitrite, and combinations thereof.

As used herein, the term "organic anion" means the conjugate base of an organic acid. As used herein, the term "organic" means a species containing a carbon-hydrogen bond. The organic anions may be selected from alcoholates, carboxylates, and combinations thereof. The alcoholate may contain 1 to 6 carbon atoms, preferably 1 to 3 carbon atoms. The carboxylate may contain 1 to 18 carbon atoms. Preferably, the carboxylate may be selected from acetate, citrate, hydrogencitrate, formate, lactate, tartrate, and combinations thereof. More preferably, the carboxylate may be selected from acetate, formate, citrate, and combinations thereof.

The inorganic carboxylate may be selected from oxalate, carbamate, and combinations thereof. Preferably, the anion may be one or more nitrate, nitrite, or acetate anions, most preferably nitrate anions.

In this first embodiment, the salt may be present in the treatment solution in a concentration of less than 0.015 molar (moles of salt per liter of treatment solution), preferably less than 0.01 molar, more preferably less than 0.007 molar, most preferably at most 0.005 molar, in particular at most 0.004 molar. The salt may be present in the treatment solution in a concentration of at least 0.0001 molar, preferably at least 0.001 molar, more preferably at least 0.0015 molar, and most preferably at least 0.002 molar. The salt may be present in the treatment solution in a concentration in the range of from 0.001 to 0.006 molar, preferably from 0.0015 to 0.0045 molar, more preferably from 0.002 to 0.004 molar.

In a second embodiment, the salt may comprise a cation, which may be selected from ammonium, phosphonium, organic cations and combinations thereof, and an anion, which may be selected from organic anions, inorganic carboxylates, oxyanions of elements from Groups IIIA through VIIA of the Periodic Table of Elements, and combinations thereof. The organic cation may be selected from alkyl ammoniums, carbonium, alkyl carboniums, alkyl phosphoniums, aryl phosphoniums, arylalkyl phosphoniums, and combinations thereof. The organic cation may be mono-, di-, tri-, or tetra-substituted. Each alkyl group may contain 1 to 18 carbon atoms in the molecular structure, for example methyl, ethyl, propyl, butyl, cetyl, lauryl, and stearyl. Preferably, each alkyl group may contain 1 to 12 carbon atoms in the molecular structure. Preferably, each aryl group may be a phenyl group. Preferably, the cation may be one or more ammonium or alkyl ammonium cations.

The Group IIIA through VIIA oxyanion may be selected from borate, metaborate, tetraborate, tetrafluoroborate, carbonate, hydrogencarbonate, chlorate, perchlorate, bromate, perbromate, phosphate, metaphosphate, orthophosphate, hydrogenphosphate, dihydrogenphosphate, fluorophosphates, phosphite, hydrogenphosphite, sulfate, disulfate, hydrogensulfate, thiosulfate, sulfite, disulfite, hydrogensulfite, thiosulfite, nitrate, nitrite, and combinations thereof. Preferably, the oxyanions may be of elements from Group VA, in particular phosphate, metaphosphate, orthophosphate, hydrogenphosphate, dihydrogenphosphate, fluorophosphates, phosphite, hydrogenphosphite, nitrate, nitrite, and combinations thereof.

The organic anions may be selected from alcoholates, carboxylates, and combinations thereof. The alcoholate may contain 1 to 6 carbon atoms, preferably 1 to 3 carbon atoms. The carboxylate may contain 1 to 18 carbon atoms. Preferably, the carboxylate may be selected from acetate, citrate, hydrogencitrate, formate, lactate, tartrate, and combinations thereof. More preferably, the carboxylate may be selected from acetate, formate, citrate, and combinations thereof.

The inorganic carboxylate may be selected from oxalate, carbamate, and combinations thereof. Preferably, the anion may be one or more nitrate, nitrite, or acetate anions, most preferably nitrate anions.

In this second embodiment, the salt may be present in the treatment solution in a concentration of at most 0.05 molar (moles of salt per liter of treatment solution), preferably at most 0.03 molar, more preferably less than 0.01 molar, most preferably less than 0.007 molar, in particular less than 0.005 molar, and more in particular at most 0.004 molar. The salt may be present in the treatment solution in a concentration of at least 0.0001 molar, preferably at least 0.001 molar, more preferably at least 0.0015 molar, and most preferably at least 0.002 molar. The salt may be present in the treatment solution in a concentration in the range of from 0.001 to 0.05 molar, preferably from 0.001 to 0.03 molar, more preferably from 0.0015 to 0.009, most preferably from 0.002 to 0.004 molar.

The carrier, or the precursor thereof, may be contacted prior to the treatment process with a liquid other than the treatment solution, as defined hereinbefore. The liquid may include de-ionized water, solutions having a salt concentration greater than 0.05 molar, alcohols, dilute acids, and dilute bases. The carrier, or the precursor thereof, may be contacted subsequent to the treatment process with water, an alcohol or combinations thereof.

After the contacting and separating steps, the carrier, or the precursor thereof, may then be dried. Such drying step is suitably carried out at a temperature of at most 500° C., preferably at most 300° C., more preferably at most 280° C., most preferably at most 260° C., and at a temperature of at least 180° C., preferably at least 210° C., more preferably at least 220° C. Suitably, the drying step may be for a period of time of at least 1 minute, preferably at least 2 minutes, and for a period of time of at most 60 minutes, preferably at most 30 minutes, more preferably at most 10 minutes. The carrier, or the precursor thereof, may be dried in the presence of any atmosphere, preferably nitrogen, argon, helium, and more preferably air. If a precursor of the carrier has undergone the treatment process as described hereinbefore, the precursor may then be calcined to form the carrier. Calcination methods are known in the art and typically heat the precursor to temperatures in the range of from 500° C. to 1600° C.

Catalysts which have been prepared by using a carrier, or the precursor thereof, that has been so treated have improved stability performance, in particular improved activity stability, and/or selectivity stability.

Generally, the catalyst of this invention comprises silver as a catalytically active metal. Appreciable catalytic activity is obtained by employing a silver content of the catalyst of at least 10 g/kg, in particular at least 50 g/kg, relative to the weight of the catalyst. The preparation of the catalysts is known in the art and the known methods are applicable to the preparation of the catalyst of this invention. Methods of preparing the catalyst include impregnating the carrier with a silver compound and performing a reduction to deposit metallic silver particles. Catalysts having relatively high silver content may be prepared by multiple impregnations, for example double or triple impregnation. For examples of suitable methods, reference may be made, for example, to U.S. Pat. Nos. 5,380,697, 5,739,075, 6,368,998, US-2004/0049061 A1, US-2002/0010094 A1, EP-A-266015, WO-00/15333, WO-00/15334 and WO-00/15335, which are incorporated herein by reference.

The impregnation may include impregnation with a solution of which the pH has a value above 12, for example 13 or 13.2 or above. This may be accomplished by the addition of a base to the impregnation solution, for example lithium hydroxide, cesium hydroxide or a tetraalkylammonium hydroxide, for example tetramethylammonium hydroxide or tetraethylammonium hydroxide, in sufficient quantity. Dependent of the composition of the impregnation solution, a quantity of base in the range of from 20 to 70 mmole/kg carrier, for example 30, 40, 50 or 60 mmole/kg carrier may be sufficient to achieve a sufficiently high pH.

The reduction of cationic silver to metallic silver may be accomplished during a step in which the catalyst is dried, so that the reduction as such does require a separate process step. This may be the case if the impregnation solution comprises a reducing agent, for example, an oxalate, as described in the Examples hereinafter.

The catalyst preferably comprises silver, and a further element or compound thereof. Eligible further elements may be selected from the group of nitrogen, sulfur, phosphorus, boron, fluorine, Group IA metals, Group IIA metals, rhenium, molybdenum, tungsten, chromium, titanium, hafnium, zirconium, vanadium, manganese, thallium, thorium, tantalum, niobium, gallium and germanium and combinations thereof. Preferably the Group IA metals are selected from lithium, potassium, rubidium and cesium. Most preferably the Group IA metal is lithium, potassium and/or cesium. Preferably the Group IIA metals are selected from calcium and barium. Where possible, the further element may suitably be provided as an oxyanion, for example, as a sulfate, borate, perrhenate, molybdate or nitrate, in salt or acid form.

It is preferred to employ the carrier of this invention in the preparation of a highly selective catalyst. The highly selective silver-based catalysts may comprise, in addition to silver, one or more of rhenium, molybdenum, tungsten, a Group IA metal, and a nitrate- or nitrite-forming compound, which may each be present in a quantity of from 0.01 to 500 mmole/kg, calculated as the element (rhenium, molybdenum, tungsten, the Group IA metal or nitrogen) on the total catalyst. The nitrate- or nitrite-forming compounds and particular selections of nitrate- or nitrite-forming compounds are as defined hereinafter. The nitrate- or nitrite-forming compound is in particular a Group IA metal nitrate or a Group IA metal nitrite. Rhenium, molybdenum, tungsten or the nitrate- or nitrite-forming compound may suitably be provided as an oxyanion, for example as a perrhenate, molybdate, tungstate or nitrate, in salt or acid form.

Of special preference are the highly selective catalysts which comprise rhenium in addition to silver. Such catalysts are known from EP-A-266015, U.S. Pat. Nos. 4,761,394 and 4,766,105, which are incorporated herein by reference. Broadly, they comprise silver, rhenium or a compound thereof, the further element (as defined hereinbefore, in particular tungsten, molybdenum and/or a Group IA metal, in particular lithium and/or cesium) other than rhenium or compound thereof, and optionally a rhenium co-promoter. The rhenium co-promoter may be selected from one or more of sulfur, phosphorus, boron, and compounds thereof.

Preferred amounts of the components of the catalysts are, when calculated as the element, relative to the weight of the catalyst:

silver from 10 to 500 g/kg,
rhenium from 0.01 to 50 mmole/kg, if present,
the further element or elements, if present, each from 0.1 to 500 mmole/kg, and,
the rhenium co-promoter from 0.1 to 30 mmole/kg, if present.

With respect to silver, this metal is present preferably in an amount of 50 to 500 g/kg, more preferably 100 to 400 g/kg, in particular 150 to 350 g/kg. Rhenium may preferably be present in an amount of from 0.1 to 10 mmoles/kg, more preferably 0.2 to 8 mmoles/kg. The further element or elements may each be present in a preferred amount of from 0.5 to 100 mmole/kg, more preferably 1 to 80 mmole/kg.

Although the present epoxidation process may be carried out in many ways, it is preferred to carry it out as a gas phase process, i.e. a process in which the feed is contacted in the gas phase with the catalyst which is present as a solid material, typically in a packed bed. Generally the process is carried out as a continuous process.

The olefin for use in the present epoxidation process may be any olefin, for example an aromatic olefin, for example styrene, or a di-olefin, whether conjugated or not, for example 1,9-decadiene or 1,3-butadiene. Mixtures of olefins may be used. Typically, the olefin is a monoolefin, for example 2-butene or isobutene. Preferably, the olefin is a mono-α-olefin, for example 1-butene or propylene. The most preferred olefin is ethylene.

The olefin concentration in the feed may be selected within a wide range. Typically, the olefin concentration in the feed will be at most 80 mole percent, relative to the total feed. Preferably, it will be in the range of from 0.5 to 70 mole percent, in particular from 1 to 60 mole percent, on the same basis. As used herein, the feed is considered to be the composition which is contacted with the catalyst.

The present epoxidation process may be air-based or oxygen-based, see "Kirk-Othmer Encyclopedia of Chemical Technology", 3rd edition, Volume 9, 1980, pp. 445-447. In the air-based process air or air enriched with oxygen is employed as the source of the oxidizing agent while in the oxygen-based processes high-purity (at least 95 mole percent) oxygen is employed as the source of the oxidizing agent. Presently most epoxidation plants are oxygen-based and this is a preferred embodiment of the present invention.

The oxygen concentration in the feed may be selected within a wide range. However, in practice, oxygen is generally applied at a concentration which avoids the flammable regime. Typically, the concentration of oxygen applied will be within the range of from 1 to 15 mole percent, more typically from 2 to 12 mole percent of the total feed.

In order to remain outside the flammable regime, the concentration of oxygen in the feed may be lowered as the concentration of the olefin is increased. The actual safe operating ranges depend, along with the feed composition, also on the reaction conditions such as the reaction temperature and the pressure.

A reaction modifier may be present in the feed for increasing the selectively, suppressing the undesirable oxidation of olefin or olefin oxide to carbon dioxide and water, relative to the desired formation of olefin oxide. Many organic compounds, especially organic halides and organic nitrogen compounds, may be employed as the reaction modifier. Nitrogen oxides, hydrazine, hydroxylamine or ammonia may be employed as well. It is frequently considered that under the operating conditions of olefin epoxidation the nitrogen containing reaction modifiers are precursors of nitrates or nitrites, i.e. they are so-called nitrate- or nitrite-forming compounds (cf. e.g. EP-A-3642 and U.S. Pat. No. 4,822,900, which are incorporated herein by reference).

Organic halides are the preferred reaction modifiers, in particular organic bromides, and more in particular organic chlorides. Preferred organic halides are chlorohydrocarbons or bromohydrocarbons. More preferably they are selected from the group of methyl chloride, ethyl chloride, ethylene dichloride, ethylene dibromide, vinyl chloride or a mixture thereof. Most preferred reaction modifiers are ethyl chloride and ethylene dichloride.

Suitable nitrogen oxides are of the general formula $NO_x$ wherein x is in the range of from 1 to 2, and include for example NO, $N_2O_3$ and $N_2O_4$. Suitable organic nitrogen compounds are nitro compounds, nitroso compounds, amines, nitrates and nitrites, for example nitromethane, 1-nitropropane or 2-nitropropane. In preferred embodiments, nitrate- or nitrite-forming compounds, e.g. nitrogen oxides and/or organic nitrogen compounds, are used together with an organic halide, in particular an organic chloride.

The reaction modifiers are generally effective when used in low concentration in the feed, for example up to 0.1 mole percent, relative to the total feed, for example from $0.01 \times 10^{-4}$ to 0.01 mole percent. In particular when the olefin is ethylene, it is preferred that the reaction modifier is present in the feed at a concentration of from $0.1 \times 10^{-4}$ to $50 \times 10^{-4}$ mole percent, in particular from $0.3 \times 10^{-4}$ to $30 \times 10^{-4}$ mole percent, relative to the total feed.

In addition to the olefin, oxygen and the reaction modifier, the feed may contain one or more optional components, for example carbon dioxide, inert gases and saturated hydrocarbons. Carbon dioxide is a by-product in the epoxidation process. Typically, a concentration of carbon dioxide in the feed in excess of 25 mole percent, preferably in excess of 10 mole percent, relative to the total feed, is avoided. A concentration of carbon dioxide as low as 1 mole percent or lower, relative to the total feed, may be employed. A suitable concentration of carbon dioxide may be in the range of from 0.2 to 0.8 mole percent, for example 0.5 mole percent, relative to the total feed. Inert gases, for example nitrogen or argon, may be present in the feed in a concentration of from 30 to 90 mole percent, typically from 40 to 80 mole percent. Suitable saturated hydrocarbons are methane and ethane. If saturated hydrocarbons are present, they may be present in a quantity of up to 80 mole percent, relative to the total feed, in particular up to 75 mole percent. Frequently, they are present in a quantity of at least 30 mole percent, more frequently at least 40 mole percent. Saturated hydrocarbons may be added to the feed in order to increase the oxygen flammability limit.

The epoxidation process may be carried out using reaction temperatures selected from a wide range. Preferably the reaction temperature is in the range of from 150 to 325° C., more preferably in the range of from 180 to 300° C.

The epoxidation process is preferably carried out at a reactor inlet pressure in the range of from 1000 to 3500 kPa. "GHSV" or Gas Hourly Space Velocity is the unit volume of gas at normal temperature and pressure (0° C., 1 atm, i.e. 101.3 kPa) passing over one unit volume of packed catalyst per hour. Preferably, when the epoxidation process is as a gas phase process involving a packed catalyst bed, the GHSV is in the range of from 1500 to 10000 Nl/(l.h). Preferably, the process is carried out at a work rate in the range of from 0.5 to 10 kmole olefin oxide produced per m3 of catalyst per hour, in particular 0.7 to 8 kmole olefin oxide produced per m3 of catalyst per hour, for example 5 kmole olefin oxide produced per m3 of catalyst per hour. As used herein, the work rate is the amount of the olefin oxide produced per unit volume of catalyst per hour and the selectivity is the molar quantity of the olefin oxide formed relative to the molar quantity of the olefin converted.

The olefin oxide produced may be recovered from the reaction mixture by using methods known in the art, for example by absorbing the olefin oxide from a reactor outlet stream in water and optionally recovering the olefin oxide from the aqueous solution by distillation. At least a portion of the aqueous solution containing the olefin oxide may be applied in a subsequent process for converting the olefin oxide into a 1,2-diol or a 1,2-diol ether.

The olefin oxide produced in the epoxidation process may be converted into a 1,2-diol, a 1,2-diol ether, or an alkanolamine. As this invention leads to a more attractive process for the production of the olefin oxide, it concurrently leads to a more attractive process which comprises producing the olefin oxide in accordance with the invention and the subsequent use of the obtained olefin oxide in the manufacture of the 1,2-diol, 1,2-diol ether, and/or alkanolamine.

The conversion into the 1,2-diol or the 1,2-diol ether may comprise, for example, reacting the olefin oxide with water, suitably using an acidic or a basic catalyst. For example, for making predominantly the 1,2-diol and less 1,2-diol ether, the olefin oxide may be reacted with a ten fold molar excess of water, in a liquid phase reaction in presence of an acid catalyst, e.g. 0.5-1 weight percent sulfuric acid, based on the total reaction mixture, at 50-70° C. at 1 bar absolute, or in a gas phase reaction at 130-240° C. and 20-40 bar absolute, preferably in the absence of a catalyst. If the proportion of water is lowered the proportion of 1,2-diol ethers in the reaction mixture is increased. The 1,2-diol ethers thus produced may be a di-ether, tri-ether, tetra-ether or a subsequent ether. Alternative 1,2-diol ethers may be prepared by converting the olefin oxide with an alcohol, in particular a primary alcohol, for example methanol or ethanol, by replacing at least a portion of the water by the alcohol.

The conversion into the alkanolamine may comprise, for example, reacting the olefin oxide with ammonia. Anhydrous or aqueous ammonia may be used, although anhydrous ammonia is typically used to favor the production of monoalkanolamine. For methods applicable in the conversion of the olefin oxide into the alkanolamine, reference may be made to, for example U.S. Pat. No. 4,845,296, which is incorporated herein by reference. The 1,2-diol and the 1,2-diol ether may be used in a large variety of industrial applications, for example in the fields of food, beverages, tobacco, cosmetics, thermoplastic polymers, curable resin systems, detergents, heat transfer systems, etc. The alkanolamine may be used, for example, in the treating ("sweetening") of natural gas.

Unless specified otherwise, the low-molecular weight organic compounds mentioned herein, for example the olefins, 1,2-diols, 1,2-diol ethers, alkanolamines and reaction modifiers, have typically at most 40 carbon atoms, more typically at most 20 carbon atoms, in particular at most 10 carbon atoms, more in particular at most 6 carbon atoms. As defined herein, ranges for numbers of carbon atoms (i.e. carbon number) include the numbers specified for the limits of the ranges.

Having generally described the invention, a further understanding may be obtained by reference to the following examples, which are provided for purposes of illustration only and are not intended to be limiting unless otherwise specified.

Illustrative Embodiments

In the following illustrative embodiments, two different types of alpha-alumina carriers were utilized. The nominal properties for these different types of carriers are summarized below in Table I.

TABLE I

| Carrier Properties: | Type A Carrier | Type B Carrier |
|---|---|---|
| Surface Area (m²/g) | 0.81-0.90 | 1.77-2.05 |
| Water Absorption (%) | 39-45 | 40-45 |
| Bulk Packing Density (kg/m³) | 719-787 | 743-788 |

Experiment 1:

To a 500 mL Erlenmeyer flask, 100 grams of a Type A carrier, see Table I above, was added. The flask was then heated to 100° C. in an oven. The flask was removed from the oven and 140 grams of de-ionized water, which was pre-equilibrated at a temperature of 90° C., was added to the flask. The flask containing the carrier and water was placed into a water bath at 90° C. to maintain a constant temperature. After 20 minutes, the flask was removed from the water bath and the water solution separated from the carrier by filtration. The sodium content of the water solution was measured by Flame Atomic Emission using a Perkin Elmer 3300 Atomic Absorption Spectrometer. The procedure was repeated using a contact time of 30 minutes. A reference blank was run using water and a flask without added carrier. The results are summarized below in Table II.

Experiment 2:

The procedure of Experiment 1 was repeated except that 0.00375 molar aqueous ammonium nitrate solution was substituted for de-ionized water. The results are summarized below in Table II.

Experiment 3:

The procedure of Experiment 1 was repeated except that 0.00375 molar aqueous ammonium acetate solution was substituted for de-ionized water. The results are summarized below in Table II.

TABLE II

| Treatment Solution | Quantity of Na after 20 min (ppmw) | Quantity of Na after 30 min (ppmw) |
|---|---|---|
| De-ionized Water | 24.0 | 24.2 |
| Ammonium Nitrate | 37.0 | 41.2 |
| Ammonium Acetate | 38.9 | 41.4 |

Experiments 1-3 demonstrate that a treatment solution having a low salt concentration more efficiently removes impurities, for example sodium, from the carrier as compared to de-ionized water.

EXAMPLE 1

A Type A carrier (see Table I above) and de-ionized water, in a mass ratio of water to carrier of approximately 1.4, were placed in contact in an open vessel. The pH of the de-ionized water was 5.9, as measured at 25° C. The temperature of the water was increased to 90° C. and maintained at 90° C. for approximately 2 hours. After contact, the de-ionized water was separated from the carrier. The carrier was then treated again by adding additional room temperature de-ionized water to the vessel in a mass ratio of de-ionized water to carrier of approximately 1.4. The carrier was contacted with the de-ionized water for approximately 15 minutes without heating. The water was then separated from the carrier and the carrier was dried at 250° C. for 15 minutes in flowing air.

EXAMPLE 2

A Type A carrier (see Table I above) and a treatment solution were placed in a water bath at 90° C. in separate uncovered Erlenmeyer flasks. Once equilibrated to 90° C., sufficient treatment solution was poured into the flask containing the carrier to achieve a mass ratio of treatment solution to carrier of 1.33. The temperature was maintained at 90° C. during the approximately 2 hours of contact time. After contact, the treatment solution was separated from the carrier and the carrier was then dried at 250° C. for 15 minutes in flowing air. The treatment solution utilized in this example was a 0.0625 molar aqueous ammonium nitrate solution. The pH of the 0.0625 molar aqueous ammonium nitrate solution was 5.4, as measured at 25° C.

EXAMPLE 3

A Type A carrier (see Table I above) and a treatment solution, in a mass ratio of treatment solution to carrier of approximately 1.4, were placed in contact in an open vessel. The temperature of the treatment solution was increased to 90° C. and maintained at 90° C. for approximately 1 hour. The treatment solution was a 0.00375 molar aqueous ammonium nitrate solution. The pH of the 0.00375 molar aqueous ammonium nitrate solution was 5.9, as measured at 25° C.

After contact, the treatment solution was separated from the carrier. The carrier was then treated a second time by adding additional room temperature 0.00375 molar ammonium nitrate solution to the vessel in a mass ratio of solution to carrier of approximately 1.4. The solution was allowed to contact the carrier for approximately 15 minutes without heating. The solution was then separated from the carrier. The carrier was treated a third time by adding additional room temperature 0.00375 molar ammonium nitrate solution to the vessel in a mass ratio of solution to carrier of approximately 1.4. The solution was allowed to contact the carrier for approximately 15 minutes without heating. The solution was separated from the carrier and the carrier then dried at 250° C. for 15 minutes in flowing air.

EXAMPLE 4

Stock Silver Impregnating Solution:

This describes the preparation of a stock silver impregnation solution used for impregnating various support materials as described in the following examples. In a 5-liter stainless steel beaker 415 grams of reagent grade sodium hydroxide was dissolved in 2340 ml of de-ionized water. The temperature of the solution was adjusted to about 50° C. In a 4-liter stainless steel beaker 1699 grams of silver nitrate was dissolved in 2100 ml of de-ionized water. The temperature of the solution was adjusted to about 50° C. The sodium hydroxide solution was slowly added to the silver nitrate solution with stirring while the temperature was maintained at about 50° C. The resulting slurry was stirred for about 15 minutes. The pH of the solution was maintained at above 10 by the addition of NaOH solution as required. A washing procedure was used which included removing liquid by the use of a filter wand followed by the replacement of the removed liquid with an equivalent volume of de-ionized water. This washing procedure was repeated until the conductivity of the filtrate dropped below 90 micro-mho/cm. After the completion of the last wash cycle, 1500 ml of de-ionized water was added and followed by the addition of 630 grams of oxalic acid dihydrate (4.997 moles) in increments of 100 grams while stirring and maintaining the solution at about 40° C. (±5° C.). The pH of the solution was monitored during the addition of the last 130 grams of oxalic acid dihydrate to ensure that it did not drop below 7.8 for an extended period of time. Water was removed from the solution with a filter wand and the slurry was cooled to less than 30° C. Slowly added to the solution was 732 grams of 92% ethylenediamine (EDA). The temperature was maintained below 30° C. during this addition. A spatula was used to manually stir the mixture until enough liquid was present to mechanically stir. The final solution was used as a stock silver impregnation solution for preparing the catalysts in the following examples.

The final solution was used as a stock silver impregnation solution for preparing the catalysts.

A silver catalyst was prepared on the de-ionized water treated carrier from Example 1 according to the following procedure. A silver containing impregnating solution was made by mixing 56.2 grams of silver stock solution of specific gravity 1.547 g/ml with a solution of 0.1116 g 46.07 wt % cesium hydroxide and 0.2876 g lithium hydroxide monohydrate in 2 cc water. Additional water was added to adjust the specific gravity of the solution to 1.495 g/ml. This impregnating solution was used to prepare the silver catalyst. A vessel containing 30 grams of the carrier was evacuated to 20 mm Hg for 1 minute and the final impregnation solution was added while under vacuum, then the vacuum was released and the precursor was contacted with the liquid for 3 minutes. The impregnated precursor was then centrifuged at 500 rpm for 2 minutes to remove excess liquid. The wet precursor pellets were placed in a vibrating shaker and dried in air flowing at a rate of 16.2 Nl/h at 250° C. for 5.5 minutes.

The catalyst prepared, Catalyst A (for comparison), contained 14.5 wt % silver, 60 mmole/kg lithium, and 3.4 mmole/kg cesium, all relative to the weight of the catalyst.

EXAMPLE 5

A second catalyst, Catalyst B (for comparison), was prepared in the same way as Example 4, except an ammonium nitrate treated carrier, according to Example 2, was used instead of the de-ionized water treated carrier of Example 1.

EXAMPLE 6

A third catalyst, Catalyst C (according to the invention), was prepared in the same way as Example 4, except an ammonium nitrate treated carrier, according to Example 3, was used instead of the de-ionized water treated carrier of Example 1.

EXAMPLE 7

The catalysts A, B and C were used to produce ethylene oxide from ethylene and oxygen. To do this, crushed samples of catalyst were loaded into separate stainless steel U-shaped tubes. Each tube was immersed in a molten metal bath (heat medium) and the ends were connected to a gas flow system. A gas mixture passed through the catalyst bed, in a "once-through" operation. The weight of catalyst used and the inlet gas flow rate were adjusted to give a gas hourly space velocity of 30,000 Nl/(l.h), as calculated for uncrushed catalyst. The inlet gas pressure was 1550 kPa (absolute).

The gas mixture passed through the catalyst bed, in a "once-through" operation, during the entire test run including the start-up, consisted of 30.0 volume percent ethylene, 8.0 volume percent oxygen, 5.0 volume percent carbon dioxide, 57.0 volume percent nitrogen and 5.6 parts per million by volume (ppmv) ethyl chloride.

The initial reactor temperature was 180° C., and this was increased at a rate of 10° C. per hour to 225° C. and then adjusted so as to achieve a constant oxygen conversion level of 25.0 percent during the course of the run.

Upon reaching the desired oxygen conversion level, performance data was obtained for initial selectivity and activity. For Catalysts A, B and C, the cumulative production of ethylene oxide required to cause a 0.8% decrease in selectivity as well a 1.6% decrease in selectivity, relative to the initial selectivity, was determined. Additionally, the cumulative production of ethylene oxide required to cause a 9° C. increase in temperature as well as a 14° C. increase in temperature, relative to the initial activity, was determined for Catalysts A, B and C. A higher value for the cumulative production of ethylene oxide required to cause a certain decrease in selectivity or a certain increase in temperature (i.e., a decrease in activity) signifies improved stability. Table III below summarizes the values measured. The cumulative production of ethylene oxide is represented in Table III as kiloton (kT) of ethylene oxide/$m^3$ of catalyst.

The performance data summarized in Table III, below, shows that Catalyst C, made according to this invention, exhibits improved stability at the same oxygen conversion levels as compared to comparative Catalysts A and B.

TABLE III

| Catalyst | Carrier Treatment | Cumulative EO (kT/$m^3$) for a decrease in Selectivity of 0.8% | Cumulative EO (kT/$m^3$) for a decrease in Selectivity of 1.6% | Cumulative EO (kT/$m^3$) for an increase in Temperature of 9° C. | Cumulative EO (kT/$m^3$) for an increase in Temperature of 14° C. |
|---|---|---|---|---|---|
| Catalyst A* | de-ionized water | 0.64 | 1.20 | 0.74 | 1.37 |
| Catalyst B* | 0.0625 molar ammonium nitrate solution | 0.64 | *** | 0.76 | *** |
| Catalyst C** | 0.00375 molar ammonium nitrate solution | 1.02 | 1.80 | 1.06 | 1.80 |

*for comparison
**according to the invention
*** reaction was discontinued

EXAMPLE 8

A Type B carrier was treated according to the procedure in Example 1, except that the carrier and the de-ionized water were placed in a water bath at 90° C. in separate Erlenmeyer flasks and, once equilibrated to 90° C., sufficient de-ionized water was poured into the flask containing the carrier to achieve the mass ratio of water to carrier of approximately 1.4.

EXAMPLE 9

A Type B carrier was treated with ammonium nitrate solution according to the procedure in Example 2.

EXAMPLE 10

A Type B carrier was treated with ammonium nitrate solution according to the procedure in Example 3.

EXAMPLE 11

A sample of carrier prepared according to Example 8 was impregnated with a silver containing impregnating solution. The silver containing impregnating solution was made by mixing 107.3 grams of silver stock solution of specific gravity 1.547 g/ml with a solution containing 0.1170 g of ammonium perrhenate in 2 g of 1:1 (w/w) ethylenediamine/water, 0.0544 g of ammonium metatungstate dissolved in 2 g of 1:1 ammonia/water and 0.3662 g lithium hydroxide monohydrate dissolved in water. Additional water was added to adjust the specific gravity of the solution to 1.462 g/ml. 70 grams of the resulting solution was mixed with 0.4451 g of 46.07 weight percent cesium hydroxide solution. This silver containing impregnating solution was used to prepare the silver catalyst. A vessel containing 30 grams of the carrier prepared according to Example 8 was evacuated to 20 mm Hg for 1 minute and the final impregnation solution was added while under vacuum, then the vacuum was released and the precursor allowed to contact the liquid for 3 minutes. The impregnated precursor was then centrifuged at 500 rpm for 2 minutes to remove excess liquid. The wet precursor pellets were placed in a vibrating shaker and dried in air flowing at a rate of 16.2 Nl/h at 250° C. for 5.5 minutes. The resulting catalyst composition for Catalyst D (for comparison) was 14.5 wt % Ag, 7.1 mmole Cs/kg catalyst, 2.0 mmole Re/kg catalyst, 1.0 mmole W/kg catalyst, and 40 mmole Li/kg catalyst.

EXAMPLE 12

A second catalyst, Catalyst E (for comparison) was prepared in a similar manner as Example 11. A sample of carrier prepared according to Example 9 was impregnated with a silver containing impregnating solution. The silver containing impregnating solution was made by mixing 74.4 grams of silver stock solution of specific gravity 1.547 g/ml with a solution containing 0.0811 g of ammonium perrhenate in 2 g of 1:1 (w/w) ethylenediamine/water, 0.0377 g of ammonium metatungstate dissolved in 2 g of 1:1 ammonia/water and 0.2539 g lithium hydroxide monohydrate dissolved in water. Additional water was added to adjust the specific gravity of the solution to 1.481 g/ml. 80 grams of the resulting solution was mixed with 0.3080 g of 46.07 weight percent cesium hydroxide solution. This silver containing impregnating solution was used to prepare the silver catalyst. The final Catalyst E composition was 14.8 wt % Ag, 7.1 mmole Cs/kg catalyst, 2.0 mmole Re/kg catalyst, 1.0 mmole W/kg catalyst, and 40 mmole Li/kg catalyst.

EXAMPLE 13

A third catalyst, Catalyst F (according to the invention), was prepared in a similar manner as Example 11. A sample of carrier prepared according to Example 10 was impregnated with a silver containing impregnating solution. The silver containing impregnating solution was made by mixing 107.3 grams of silver stock solution of specific gravity 1.547 g/ml with a solution containing 0.1170 g of ammonium perrhenate in 2 g of 1:1 (w/w) ethylenediamine/water, 0.0544 g of ammonium metatungstate dissolved in 2 g of 1:1 ammonia/water and 0.3662 g lithium hydroxide monohydrate dissolved in water. Additional water was added to adjust the specific gravity of the solution to 1.462 g/ml. 70 grams of the resulting solution was mixed with 0.4451 g of 46.07 weight percent cesium hydroxide solution. This silver containing impregnating solution was used to prepare the silver catalyst. The final Catalyst F composition was 14.5 wt % Ag, 7.1 mmole Cs/kg catalyst, 2.0 mmole Re/kg catalyst, 1.0 mmole W/kg catalyst, and 40 mmole Li/kg catalyst.

EXAMPLE 14

Catalysts D, E and F were tested in the production of ethylene oxide from ethylene and oxygen. To do this, an amount of crushed catalysts D, E and F were each loaded into separate stainless steel U-shaped tubes. Each tube was immersed in a molten metal bath (heat medium) and the ends were connected to a gas flow system. A gas mixture passed through the catalyst bed, in a "once-through" operation. The weight of the catalyst used and the inlet gas flow rate were adjusted to give a gas hourly space velocity of 27,200 Nml of gas per ml catalyst per hour, as calculated for uncrushed catalyst. The inlet gas pressure was 1550 kPa (absolute).

The gas mixture contained 30% v ethylene, 8% v oxygen, 5% v carbon dioxide, 2.4 to 5 ppmv ethyl chloride, and nitrogen balance.

The initial reactor temperature was 200° C., and this was increased to 230° C. over a period of approximately 24 hours. The temperature was then adjusted so as to achieve an ethylene oxide content of 1.5% v in the outlet gas stream. The temperature was slowly increased to compensate for a decline in catalyst performance as a result of aging, i.e., such that a constant ethylene oxide content in the outlet gas stream was maintained.

Upon reaching the desired ethylene oxide content in the outlet gas stream, performance data was obtained for initial selectivity and activity. For Catalysts D, E and F, the cumulative production of ethylene oxide required to cause a 2.5% decrease in selectivity, relative to the initial selectivity, was determined. Additionally, the cumulative production of ethylene oxide required to cause a 30° C. increase in temperature, relative to the initial activity, was determined for Catalysts D, E and F. A higher value for the cumulative production of ethylene oxide required to cause a certain decrease in selectivity or a certain increase in temperature (i.e., a decrease in activity) signifies improved stability. Table IV below summarizes the values measured. The cumulative production of ethylene oxide is represented in Table IV as kiloton (kT) of ethylene oxide/$m^3$ of catalyst.

The performance data summarized in Table IV, below, shows that Catalyst F, made according to this invention, exhibits improved stability at the same ethylene oxide production levels as compared to comparative Catalysts D and E.

TABLE IV

| Catalyst | Carrier Treatment | Cumulative EO (kT/$m^3$) for a decrease in Selectivity of 2.5% | Cumulative EO (kT/$m^3$) for an increase in Temperature of 30° C. |
|---|---|---|---|
| Catalyst D* | de-ionized water | 0.63 | 0.49 |
| Catalyst E* | 0.0625 molar ammonium nitrate solution | 0.50 | 0.44 |
| Catalyst F** | 0.00375 molar ammonium nitrate solution | 0.71 | 0.64 |

*for comparison
**according to the invention

What is claimed is:

1. A process for treating an alumina carrier, or a precursor thereof, to at least partly remove impurities from the alumina carrier, or the precursor thereof, comprising:
    contacting the alumina carrier, or the precursor thereof, with a treatment solution comprising a salt in a concentration of from 0.0001 molar to 0.05 molar at a temperature of greater than 40° C. wherein the salt comprises a cation and an anion, and wherein the cation is selected from ammonium, organic cations and combinations thereof, and wherein the anion is selected from organic anions, inorganic carboxylates, oxyanions of elements from Groups IIIA through VIIA of the Periodic Table of Elements, and combinations thereof; and
    separating at least part of the treatment solution from the alumina carrier, or the precursor thereof.

2. The process as claimed in claim 1, wherein the anion is an oxyanion selected from borate, metaborate, tetraborate, tetrafluoroborate, carbonate, hydrogencarbonate, chlorate, perchlorate, bromate, perbromate, phosphate, metaphosphate, orthophosphate, hydrogenphosphate, dihydrogenphosphate, fluorophosphates, phosphite, hydrogenphosphite, sulfate, disulfate, hydrogensulfate, thiosulfate, sulfite, disulfite, hydrogensulfite, thiosulfite, nitrate, nitrite, and combinations thereof.

3. The process as claimed in claim 1, wherein the anion is selected from nitrate, nitrite, acetate and combination thereof.

4. The process as claimed in claim 1, wherein the anion is nitrate.

5. The process as claimed in claim 1, wherein the cation is an alkyl ammonium cation.

6. The process as claimed in claim 1, wherein the cation is ammonium.

7. The process as claimed in claim 1, wherein the concentration of the salt is at most 0.03 molar.

8. The process as claimed in claim 1, wherein the concentration of the salt is in the range of from 0.001 to 0.03 molar.

9. The process as claimed in claim 1, wherein the concentration of the salt is in the range of from 0.0015 to 0.009 molar, and the mass ratio of the treatment solution to the alumina carrier, or the precursor thereof, is at least 1.25.

10. The process as claimed in claim 1, wherein the process further comprises contacting the alumina carrier, or the precursor thereof, with the treatment solution for at least 5 minutes at a temperature in the range of from 75° C. to 120° C., and subsequently drying the alumina carrier, or the precursor thereof, at a temperature of at most 500° C.

11. The process as claimed in claim 1, wherein the process further comprises:
    subsequently contacting the alumina carrier, or the precursor thereof, with an additional treatment solution comprising a salt, wherein the salt comprises an anion and a cation; and
    separating at least part of the additional treatment solution from the alumina carrier, or the precursor thereof.

12. A process for preparing a catalyst comprising:
    contacting an alumina carrier, or a precursor thereof, with a treatment solution comprising a salt in a concentration of from 0.0001 molar to 0.05 molar at a temperature of greater than 40° C., wherein the salt comprises a cation and an anion, and wherein the cation is selected from ammonium, organic cations and combinations thereof, and wherein the anion is selected from organic anions, inorganic carboxylates, oxyanions of elements from Group IIIA through VIIA of the Periodic Table of Elements, and combinations thereof;
    separating at least part of the treatment solution from the alumina carrier, or the precursor thereof; and
    subsequently depositing silver on the alumina carrier.

13. The process as claimed in claim 12, wherein silver is deposited on the alumina carrier in a quantity of from 10 to 500 g/kg, relative to the weight of the catalyst.

14. The process as claimed in claim 12, wherein the process further comprises depositing on the alumina carrier one or more further elements selected from nitrogen, sulfur, phosphorus, boron, fluorine, Group IA metals, Group IIA metals, rhenium, molybdenum, tungsten, chromium, titanium, hafnium, zirconium, vanadium, manganese, thallium, thorium, tantalum, niobium, gallium, germanium combinations thereof.

15. The process as claimed in claim 12, wherein the process further comprises depositing on the alumina carrier one or more of rhenium, molybdenum, tungsten, Group IA metals, nitrate-forming compounds, nitrite-forming compounds, and combinations thereof.

16. A process for preparing ethylene oxide comprising:
    preparing the catalyst according to the process as claimed in claim 12; and
    reacting ethylene with oxygen in the presence of the catalyst.

17. The process as claimed in claim 16, wherein the process further comprises:
    converting ethylene oxide into ethylene glycol ethylene glycol ether, or ethanol amine.

* * * * *